United States Patent
Kaiser et al.

(10) Patent No.: US 10,131,876 B2
(45) Date of Patent: Nov. 20, 2018

(54) METHOD FOR AUTOMATED GENERATION OF GENETICALLY MODIFIED T CELLS

(71) Applicant: Miltenyi Biotec GmbH, Bergisch Gladbach (DE)

(72) Inventors: Andrew Kaiser, Rosrath (DE); Mario Assenmacher, Bergisch Gladbach (DE); Ian Johnston, Rosrath (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

(21) Appl. No.: 15/305,597

(22) PCT Filed: Apr. 23, 2015

(86) PCT No.: PCT/EP2015/058817
§ 371 (c)(1),
(2) Date: Oct. 20, 2016

(87) PCT Pub. No.: WO2015/162211
PCT Pub. Date: Oct. 29, 2015

(65) Prior Publication Data
US 2017/0037370 A1 Feb. 9, 2017

Related U.S. Application Data

(60) Provisional application No. 61/983,543, filed on Apr. 24, 2014.

(51) Int. Cl.
*C12N 5/0783* (2010.01)
*C12N 5/00* (2006.01)

(52) U.S. Cl.
CPC ......... *C12N 5/0636* (2013.01); *C12N 5/0087* (2013.01); *C12N 2501/51* (2013.01); *C12N 2501/515* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,572,631 | B2 | 8/2009 | Berenson et al. |
| 2011/0003380 | A1* | 1/2011 | Miltenyi ............. A61M 1/3693 435/325 |

FOREIGN PATENT DOCUMENTS

| | | |
|---|---|---|
| EP | 2594632 | 5/2013 |
| EP | 2711418 | 3/2014 |
| WO | WO 2005/108589 | 11/2005 |
| WO | WO 2009/072003 | 6/2009 |
| WO | WO 2014/048920 | 4/2014 |
| WO | WO 2015/162211 | 10/2015 |

OTHER PUBLICATIONS

Casati, A. et al., "Enrichment, stimulation, and viral trasnduction of naive and central memory CD8+ T cells under GMP conditions for translational research towards the development of adoptive cell therapy of cancer patients", MACS&more, Feb. 2012, vol. 15: pp. 20-24.*
Apel et al., "Integrated Clinical Scale Manufacturing System for Cellular Products Derived by Magnetic Cell Separation, Centrifugation and Cell Culture", Chemie Ingenieur Technik, 2013, 85(1-2):103-110, XP055211907.
Hong Zhan et al., "Production and First-In-Man Use of T Cells Engineered to Express a HSVTK-CD34 Sort Suicide Gene", PLoS One Oct. 2013, 8(10):e77106, XP055211894.
International Search Report and Written Opinion issued in PCT/EP2015/058817, dated Sep. 16, 2015.
Kaiser et al., "Towards a commercial process for the manufacture of genetically modified T cells for therapy", Cancer Gene Therapy, Mar. 2015, 22(2): 72-78, XP055211554.
Robinet et al., "A Closed Culture System for the Ex Vivo Transduction and Expansion of Human T. Lymphocytes", Journal of Hematotherapy Jun. 1998, 7(3): 205-215.
Tumaini et al., "Simplified process for the production of anti-CD19-CAR engineered T cells", Cytotherapy, Nov. 2013, 15(11): 1406-1415, XP055211897.
Wang et al., "Manufacture of tumor-and virus-specific T lymphocytes for adoptive cell therapies", Cancer Gene Therapy Mar. 2015, 22(2): 85-94, XP055211914.
Wang et al., "Phenotypic and Functional Attributes of Lentivirus-modified CD19-specific Human CD8+ Central Memory Central Memory T Cells Manufactured at Clinical Scale", Journal of Immunotherapy, Nov. 2012, 35(9): 689-701, XP055211902 (2012).
Ma et al., "Cell density plays a critical role in ex vivo expansion of T cells for adoptive immunotherapy", J. Biomed and Biotechnol. vol. 2010, Article 386545, 13 pages.

* cited by examiner

*Primary Examiner* — Michael Burkhart
(74) *Attorney, Agent, or Firm* — Fish & Richardson P.C.

(57) ABSTRACT

The present invention provides a process for generation of genetically modified T cells, T cell subsets and/or T cell progenitors comprising the steps: a) providing a cell sample comprising T cells, T cell subsets and/or T cell progenitors b) preparation of the cell sample by centrifugation c) magnetic separation of the T cells, T cell subsets and/or T cell progenitors d) activation of the enriched T cells, T cell subsets and/or T cell progenitors using modulatory agents e) genetic modification of the T cells, T cell subsets and/or T cell progenitors f) expansion of the genetically modified T cells, T cell subsets and/or T cell progenitors in a cultivation chamber g) washing of the cultured T cells, T cell subsets and/or T cell progenitors characterized in that all steps are performed in a closed and sterile cell culture system.

16 Claims, 11 Drawing Sheets

METHOD FOR AUTOMATED GENERATION OF GENETICALLY MODIFIED T CELLS

CROSS-REFERENCE TO RELATED APPLICATIONS

This application is a 371 U.S. National Stage Application of PCT Application No. PCT/EP2015/058817, filed on Apr. 23, 2015, which claims the benefit of priority under 35 U.S.C. § 119(e) to U.S. Application No. 61/983,543, filed on Apr. 24, 2014, the entire contents of which are incorporated herein by reference.

FIELD OF THE INVENTION

The invention relates to the automated generation of modified T cells

BACKGROUND

The clinical manufacture of gene-modified T cells is currently a complex process that generally starts with obtaining the patient's peripheral blood mononuclear cells (PBMC). Current protocols feature a leukapheresis step, trading off an initially more cumbersome process (as opposed to a smaller volume blood draw) for an increased cell yield. PBMC are often enriched for T cells and activated prior to gene modification with viral or nonviral vectors. The modified T cells are then expanded in order to reach the cell numbers required for treatment, after which the cells are finally formulated and/or cryopreserved prior to reinfusion. The cell product must be subjected to a number of quality control assays and has to meet all release criteria and Good Manufacturing Practices (GMP) guidelines. Thus far, adoptive cell transfer (ACT) using gene-modified T cells has mainly been carried out by investigators who have developed their manufacturing process for small scale clinical trials by using the devices and infrastructure at hand. Such individualized therapies are complex: the cell manufacturing process is labor intensive, as it comprises many (open) handling steps (e.g., density gradient cell processing, gene modification, washing, feeding and so on) that require interventions from committed skilled operators who have undergone extensive training. The failure rate can be high owing to the high skill and time demands on clean room personnel to make these complex products. Moreover, dedicated infrastructure with clean rooms and all required instruments must be in place, qualified and functional to ensure aseptic and sterile containment. These requirements restrict such clinical manufacturing to a limited number of institutions worldwide. This in turn confines the number of runs and therefore the number of patients that can be served at any given time. Such unfavorable commercial distribution models impede investment and therefore the broad development of these promising therapies for the patients that need them (Kaiser A D, Cancer Gene Therapy (2015), 1-7).

Therefore, there is a need in the art for a method of generating gene-modified T cells for clinical use which is more robust and independent from the skills of the operators.

SUMMARY OF THE INVENTION

Generally, it is difficult to automate biological processes, especially when multiple processes must be combined in order to generate a complex product such as gene-modified T cells. Therefore, surprisingly it was found that the implementation of an automated process of generating genetically modified T cells in a device suitable for cell processing in a closed GMP-compliant environment (a closed and sterile cell culture system) is robust and leads to equal or even higher amounts of genetically modified T cells suitable for clinical application compared to non-automated processes. The invention discloses how to obtain better transduction efficiency and robust manufacturing of clinically relevant numbers of gene-modified T cells thanks to fewer manipulations inherent to the automation and the more "gentle" handling of the cells.

Cell processing in a closed GMP-compliant system may be performed e.g. with the CliniMACS Prodigy® and associated tubing sets (Miltenyi Biotec GmbH, Germany). The CliniMACS Prodigy® offers a flexible platform for cell processing applications enabling the magnetic separation of different cell types as well as cell processing protocols. Details of the sample processing system are also disclosed in WO2009/072003.

The method of the present invention comprises the automated cell preparation, selection (separation) of T cells, T cell subsets or T cell progenitors, activation of said cells, expansion of said cells, transduction of said cells, and formulation (wash) of said cells, e.g. for subsequent clinical use.

DETAILED DESCRIPTION OF THE INVENTION

Figure 6:
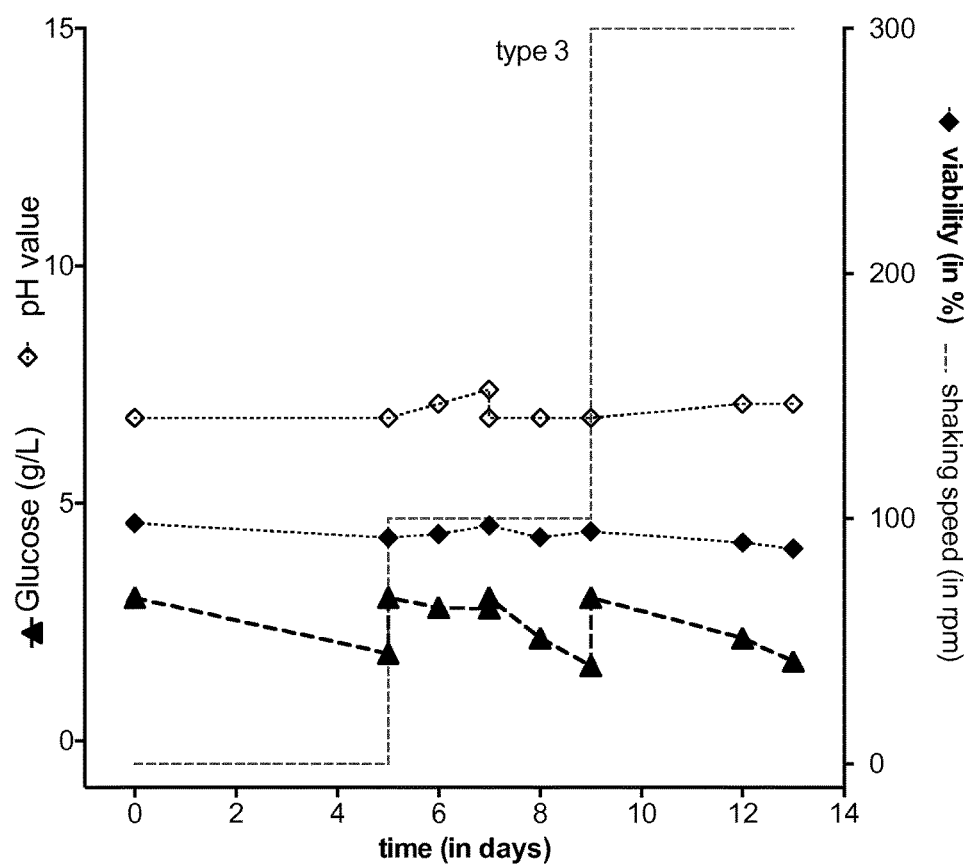
FIG. 6: In process monitoring of an automated manufacturing run FIG. 7A, B: Transduction efficiency in manual versus automated conditions
Figure 8:
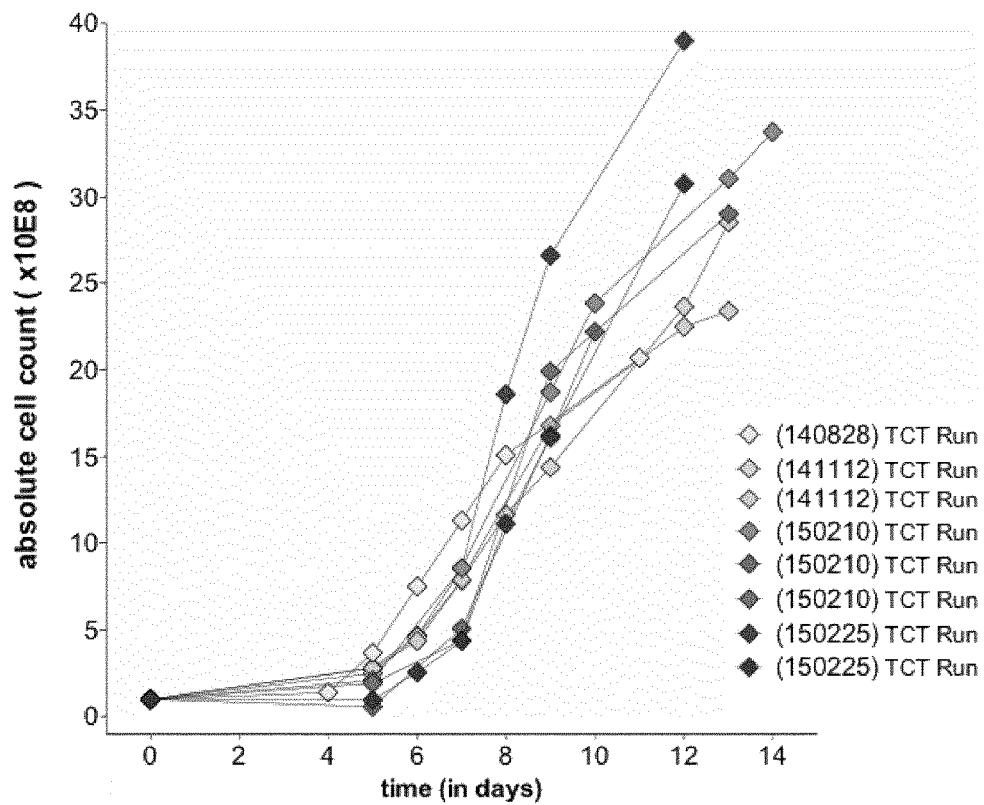
FIG. 8: Robustness of automated T cell manufacturing FIG. 9A, B: Automated manufacturing using shaking conditions on day 0

The current state of the art for the manufacturing of gene-modified T cells consists in using a large number of devices to perform small steps of the manufacturing of gene-modified T cells. Many steps require manual interventions increasing the risks of error. Here, all steps are performed in a single device, exemplarily, the CliniMACS Prodigy® is used, using a single use closed and sterile tubing set and programmed software. Surprisingly the method of the invention leads to higher transduction efficiency of the manufactured T cells and a higher transgene expression by the gene modified T cells compared to the manual process (FIG. 8). Moreover a large number of highly viable T cells can be generated robustly over less than 2 weeks (FIGS. 8 and 6). These advantages linked to the method of the invention disclosed herein rely on a highly maintained environment (temperature and gas) during the entire process as the cells do not need to be removed from an incubator for sampling for example (which would otherwise lead to a strong drop in temperature of the culture) and thanks to the gentle processing and handling of the cells in the tubing set and the absence of manual pipetting and/or use of syringes that create shear forces that are difficult to control in intensity and to normalize and are harmful to the cells and the process.

In one aspect the present invention provides an automated process (method) for generation of genetically modified T cells, T cell subsets and/or T cell progenitors comprising the steps:
a) providing a cell sample comprising T cells, T cell subsets and/or T cell progenitors
b) preparation of the cell sample by centrifugation
c) magnetic separation of the T cells, T cell subsets and/or T cell progenitors
d) activation of the enriched T cells, T cell subsets and/or T cell progenitors using modulatory agents
e) genetic modification of the T cells, T cell subsets and/or T cell progenitors
f) expansion of the genetically modified T cells, T cell subsets and/or T cell progenitors in a cultivation chamber
g) washing of the cultured T cells
characterized in that all steps are performed in a closed and sterile cell culture system.

Said magnetic separation of the T cells, T cell subsets and/or T cell progenitors may be performed by using antigen-binding molecules specific for a cell surface marker on the surface of the T cells, T cell subsets and/or T cell progenitors such as markers CD2, CD3, CD4, CD8 CD25, CD28, CD27, CD45RA, CD45RO, CD62L, CD95, CD127, CD137, alpha/beta TCR, gamma/delta TCR, CCR7, PD-1 or Lag3.

Said modulatory agents may be selected from the group consisting of agonistic antibodies, cytokines, recombinant costimulatory molecules and small drug inhibitors. Preferentially, said modulatory agents are anti-CD3 and anti-CD28 antibodies or fragments thereof coupled to beads or nanostructures. More preferentially, the modulatory agents are a nanomatrix, the nanomatrix comprising a) a matrix of mobile polymer chains, and b) attached to said matrix of mobile polymer chains anti-CD3 and anti-CD28 antibodies or fragments thereof, wherein the nanomatrix is 1 to 500 nm in size. The anti-CD3 and anti-CD28 antibodies or fragments thereof may be attached to the same or to separate matrices of mobile polymer chains. If the anti-CD3 and anti-CD28 antibodies or fragments thereof are attached to separate matrices of mobile polymer chains, fine-tuning of nanomatrices for the stimulation of the T cells is possible. The nanomatrix may be biodegradable.

In addition sterile filtration of said small nanomatrices as disclosed e.g. in WO2014/048920A1 is possible which is an important feature for long term T cell in vitro expansion under conditions which are compliant with rigorous GMP standards, i.e. in a closed and sterile cell culture system.

Said genetic modification of T cells, T cell subsets and/or T cell progenitors may be performed by transduction, transfection or electroporation.

Preferably, transduction is performed with lentiviruses, gamma-, alpha-retroviruses or adenoviruses or with electroporation or transfection by nucleic acids (DNA, mRNA, miRNA, antagomirs, ODNs), proteins, site-specific nucleases (zinc finger nucleases, TALENs, CRISP/R), self replicating RNA viruses (e.g. equine encephalopathy virus) or integration-deficient lentiviral vectors.

More preferentially, said genetic modification of T cells, T cell subsets and/or T cell progenitors may be performed by transducing said cells with lentiviral vectors.

Said expansion of the genetically modified T cells, T cell subsets and/or T cell progenitors may be performed by adding a suited cell medium for cell culture expansion such as TexMACS GMP Medium (Miltenyi Biotec GmbH) to said cultivation chamber.

Said activation, genetic modification and/or said expansion of T cells, T cell subsets and/or T cell progenitors may be performed by shaking conditions. Preferentially the shaking is performed during expansion of T cells, T cell subsets and/or T cell progenitors. Preferentially, the shaking (rotating) in the cultivation chamber takes place sporadically or periodically by rotating the cultivation chamber (centrifugation chamber) every 1-120 seconds, more preferably every 15-60 seconds and most preferably every 30 seconds, with centrifugal forces between larger (>) 0 and maximum 70×g (1 to 1000 rpm in a chamber having a radius of 6 cm) in one or two directions, more preferentially between 0.2 and 17×g (50 to 500 rpm in a chamber having a radius of 6 cm) in one or two directions, most preferentially at at 6×g (300 rpm in a chamber having a radius of 6 cm) in two directions. Importantly, the shaking conditions can be adapted during the culture (typically increased with increased cell density) to best support the T cell expansion.

Said activation may be performed by using cell densities between $0.2e^6$/ml cells to $4e^6$/ml cells to be activated and preferably between $0.5e^6$/ml cells to $2e^6$/ml and most preferably $1e^6$ cells/ml. Alternatively, said activation may be performed by using high cell densities between $4e^6$/ml cells to $2e^7$/ml cells to be activated and preferably between $4e^6$/ml cells to $1e^7$/ml.

Conventionally T cells are activated and expanded at low density under low T cell density (i.e <$1e^6$ T cells/ml or <$2e^6$ PBMC cells/ml). Normally, high T cell densities (>$3e^6$ T cells/ml or $5e^6$ PBMC cells/ml) cannot be activated properly. Therefore surprisingly, synergistic effects can be observed when high T cell, T cell subsets and/or T cell progenitor densities are activated and then expanded under shaking conditions (possibly before or after genetic modification of said cells) within the process of the present invention. This rapidly leads to very high cell numbers of genetically-modified cells (see FIG. 9). Due to this unexpected synergistic effect of the combination of activating high cell numbers e.g. with a soluble nanomatrix as mentioned above and the shaking condition during the expansion, the automated process allows to generate high numbers of modified T cells, T cell subsets and/or T cell progenitors for use in therapy in a reduced time compared to methods known in the art (i.e. 8 days instead of 14-28).

Said genetically modified T cells, T cell subsets and/or T cell progenitors may be genetically modified to express a chimeric antigen receptor (CAR), a T cell receptor (TCR), or any accessory molecule, on their cell surface.

For final formulation, the expanded and genetically modified T cells, T cell subsets and/or T cell progenitors are washed by centrifugation and replacement of culture medium with a buffer appropriate for subsequent applications such as infusion of the generated cell composition into a patient.

When required, genetically-modified T cells, T cell subsets and/or T cell progenitors can be separated from non-modified T cells e.g. using again the magnetic separation technology integrated into the closed and sterile cell culture system used.

Figure 10:
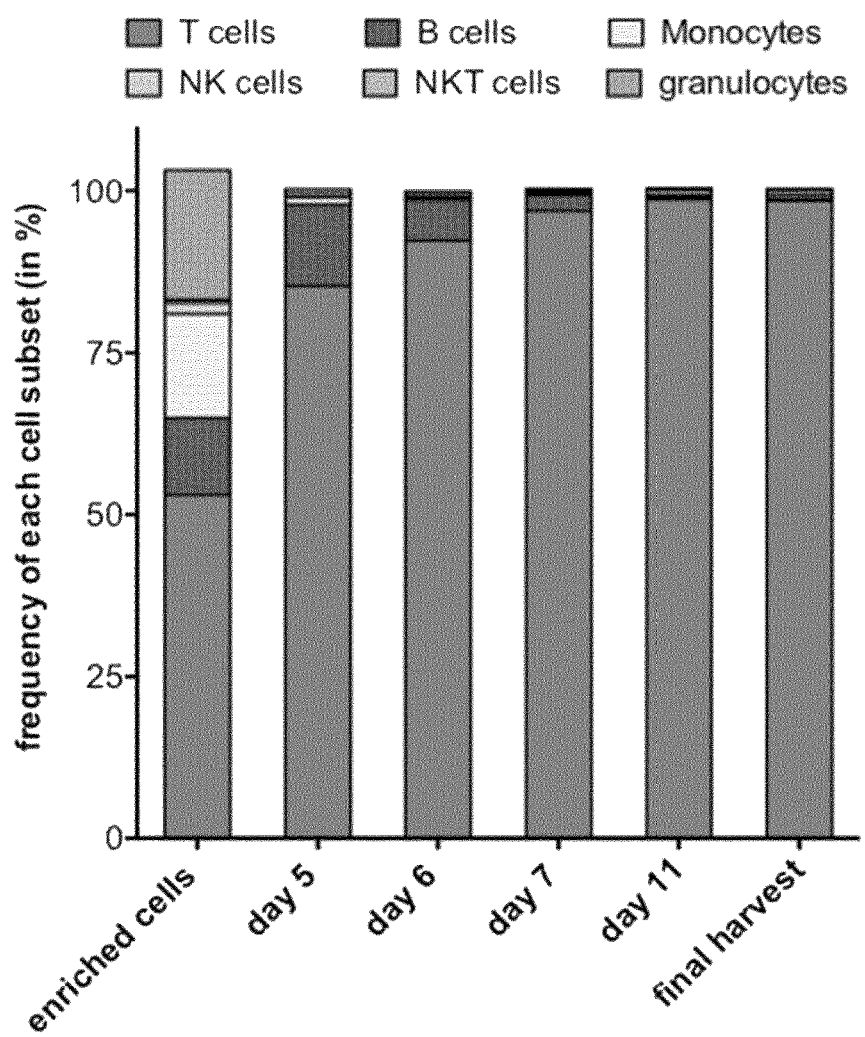
FIG. 10: Composition of the cell culture during automated manufacturing

In another aspect, the invention provides a substantially pure composition of genetically modified T cells, T cell subsets and/or T cell progenitors obtainable by the method of the present invention (see FIG. 10).

In a further aspect the invention provides a pharmaceutical composition of genetically modified T cells, T cell subsets and/or T cell progenitors obtainable by the method of the present invention.

Exemplarily the CliniMACS Prodigy® and associated tubing sets (Miltenyi Biotec GmbH, Germany) are used herein as a closed cell sample processing system on which an automated process was implemented. This system is disclosed in WO2009/072003 in detail. But it is not intended to restrict the use of the method of the present invention to the CliniMACS Prodigy® system The CliniMACS Prodigy® System is designed to automate and standardize complete cellular product manufacturing processes. It combines CliniMACS® Separation Technology (Miltenyi Biotec GmbH, Germany) with a wide range of sensor-controlled, cell processing capabilities. Prominent features of the device are:

- disposable CentriCult™ Chamber enabling standardized cell processing and cultivation
- Cell enrichment and depletion capabilities, alone or combined with CliniMACS® Reagents (Miltenyi Biotec GmbH)
- Cell cultivation and cell expansion capabilities thanks to temperature and controlled CO2 gas exchange.
- Final product formulation in pre-defined medium and volume
- the possibility to program the device using Flexible Programming Suite (FPS) and GAMP5 compatible programming language for customization of cell processing
- Tailor-made tubing sets for a variety of applications The step of separation of T cells, T cell subsets and/or T cell progenitors may comprise one, several (two or more) or a combination of positive enrichment steps, i.e. separation of T cells, T cell subsets and/or T cell progenitors (direct magnetic labeling). T cells may be selected for CD4+ and/or CD8+ T cells by using antigen binding molecules coupled to particles such as magnetic beads specific for CD4 and CD8, respectively. A subpopulation of T cells such as naïve and central memory T cells may be separated e.g. by using the marker CD62L.

The step of separation of T cells, T cell subsets and/or T cell progenitors may also comprise negative enrichment (direct labeling of non-T cells) of T cells or of the depletion of cellular subsets to be removed from the preparation. For example B cells may be removed from lymphoma patient material via the CD19 marker. Inhibitory cells such as regulatory T cells (CD25 high), monocyte (CD14) can be removed as well using the markers CD25 and CD14, respectively.

Viral transduction of the T cells can be enhanced by the use of transduction enhancer reagents, especially transduction enhancer reagents selected from the group of polycationic reagents (polybrene, protamine sulphate, poly-L-lysine, peptides with a net positive charge), poloxamers, adhesion molecules such as fibronectin or modified fibronectin (RetroNectin), or protein targeting domains such as antibodies, antibody complexes, magnetic particles.

The transduction enhancers can be provided in solution, coated on the cultivation chamber or coated on a carrier substance present in suspension/solution within the cultivation chamber.

The centrifugation chamber and the cultivation chamber may be identical. The centrifugation chamber and the cultivation chamber can be used in various conditions: for example, for separation or transduction, high rotational speed (i.e. high g-forces) can be applied, whereas for example, culturing steps may be performed with slow rotation or even at idle state. In another variant of the invention, the chamber changes direction of rotation in an oscillating manner that results in a shaking of the chamber and maintenance of the cell in suspension. Accordingly, in the process of the invention, T cell activation, gene modifying and/or cultivation steps can be performed under steady or shaking conditions of the centrifugation or the cultivation chamber.

Figure 1:
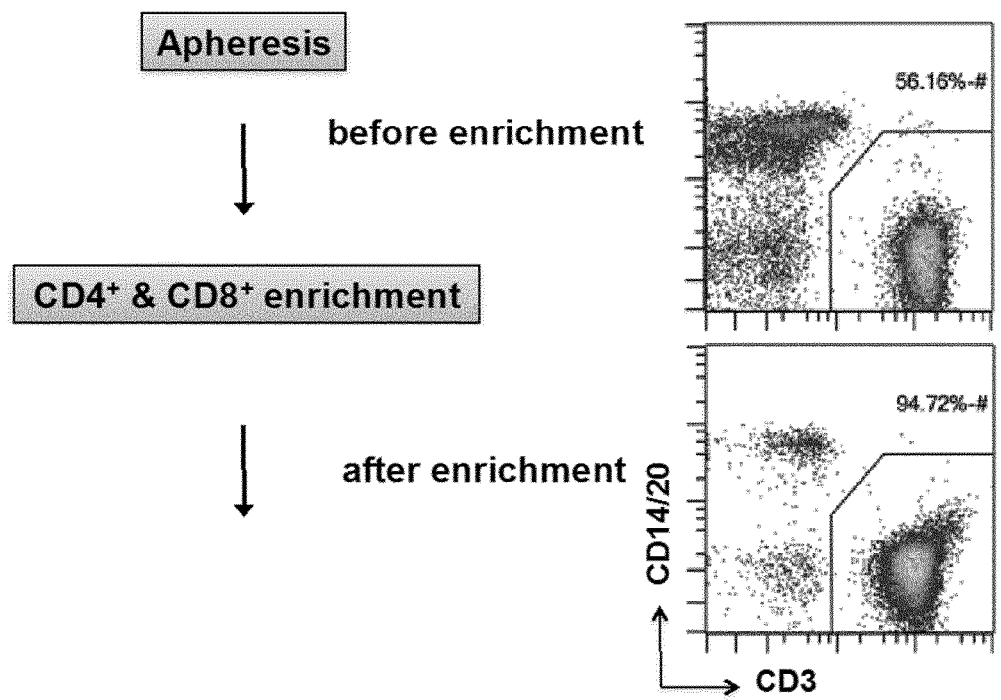
FIG. 1: Results from a representative automated T cell enrichment

FIG. 1 shows the results from a representative automated T cell enrichment. A leukapharesis of $8e^9$ total cells is connected by sterile welding to a tubing set fitted onto the CliniMACS Prodigy®. The cells are washed and labeled with CD4 and CD8 CliniMACS reagent. Labeled T cells are specifically isolated from the rest of the cells by magnetic enrichment. Cells before and after enrichment are labeled with fluorochrome-bound antibodies against CD3, CD14 and CD20 and analyzed by flow cytometry. The Top dot plot shows the composition of the cells before enrichment and the bottom dot plot represents the purity (94.7%) of the T cells after enrichment.

Figure 2:
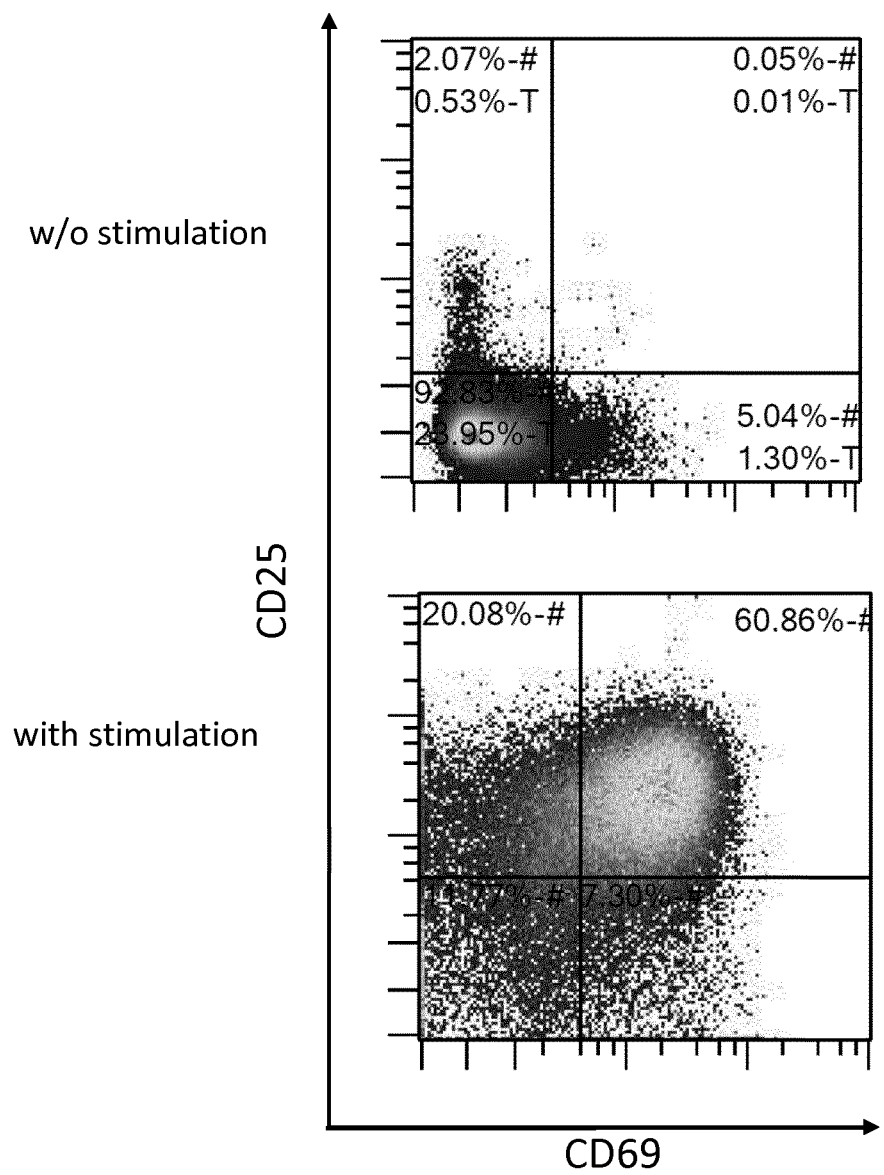
FIG. 2: Automated T cell activation

FIG. 2 to shows an automated T cell activation. On day 0, $1e^8$ enriched T cells were automatically sampled into the chamber of a tubing set on the CliniMACS Prodigy® device. The same day, the T cells are incubated with the activation reagent of MACS GMP TransAct CD3/CD28 Kit (Miltenyi Biotec GmbH) which leads to the upregulation of early activation markers CD25 and CD69. The figure represents the results from a representative flow cytometric analysis gated on live T cells before activation (top) and 24 hours after providing the activation reagent (bottom) and shows a strong upregulation of CD25 and CD69.

Figure 3:
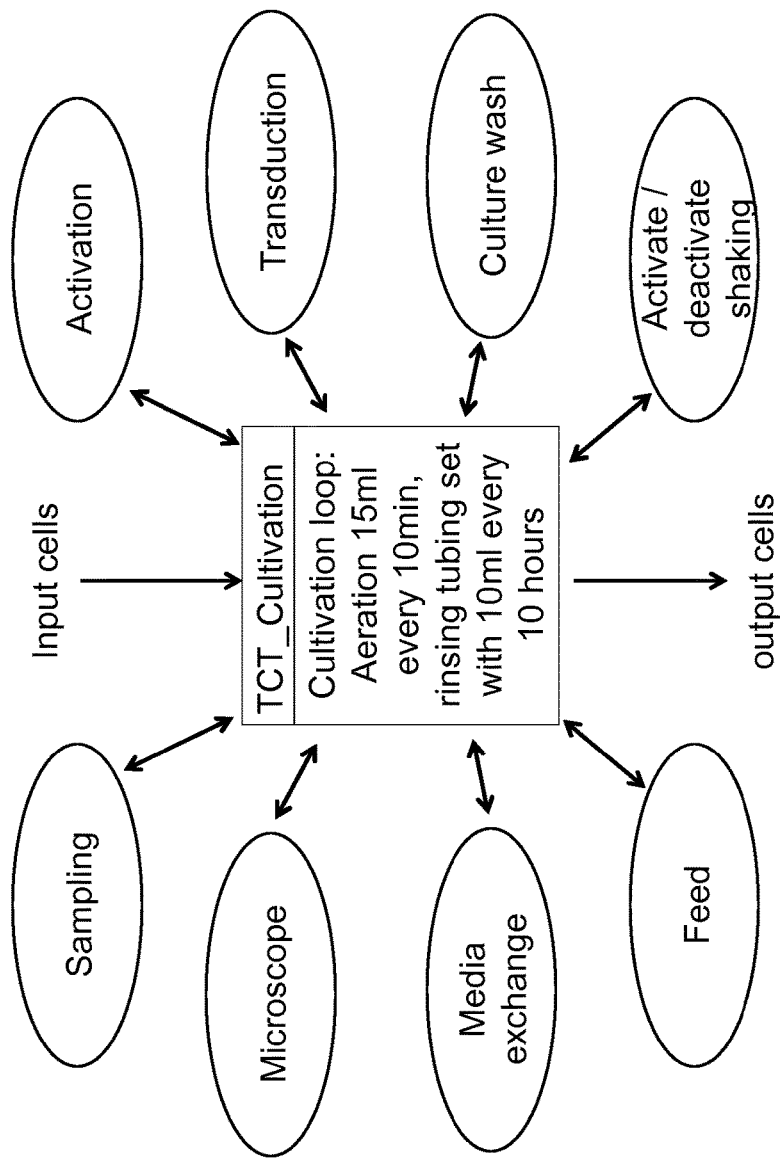
FIG. 3: Schematic representation of the software architecture allowing automated manufacturing of gene modified T cells FIG. 4A, B, C: Impact of culture shaking during the manufacturing of gene-engineered T cell

FIG. 3 shows a schematic representation of the software architecture allowing automated manufacturing of gene modified T cells: In order to perform automated manufacturing of gene engineered T cells, meaning in order to be able to automate a complicated biological process it is important to create a software capable of accepting parameters such as number of cells, flow speed, volume, temperature, % $CO_2$, motion of culture, time of incubation, medium exchange etc. For development purposes, the program must be flexible, however, for clinical use, the numbers of input parameters must be reduced and in process changes must be abrogated. Therefore we describe a program in which culture parameters, time and days when actions must take place is first set up in a so called activity matrix. The activity matrix provides guidance for the program running in the background. The background program functions as a cultivation loop (central box) controlling basic functions of the culture where "satellite programs such as "Transduction", "Reagent wash", "Feed" can be activated at defined time. Upon completion of the satellite programs, the central cultivation loop is resumed. Cultivation loop and satellite program parameters are defined in the activity matrix (input part not shown) at the initiation of the manufacturing process. Although the creation of a program is important to perform automated procedures of the process as disclosed herein the implementation of such a program can be performed by a skilled person in the art without inventive input. However the parameter input and development of the program (such as shaking modes, times and frequency) must be specifically implemented in order to obtain a robust and functional automated process (meaning a process capable of generating reliable and reproducible results with highly variable input material such as cells from patient from different medical indications).

Figure 4A:
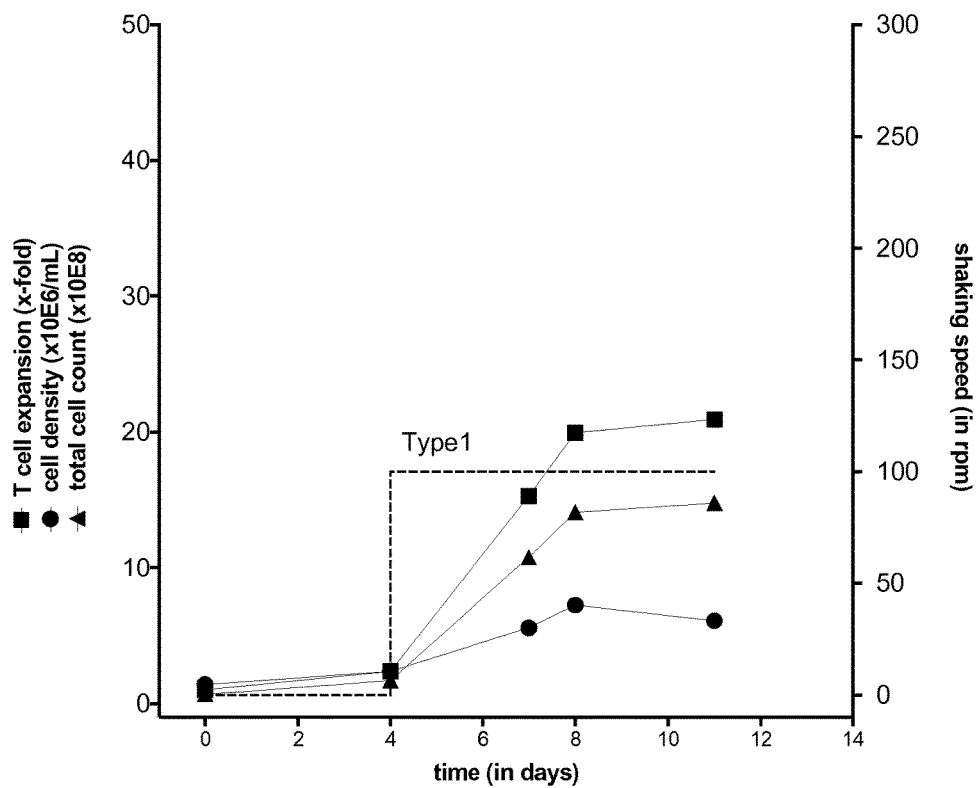
Figure 4B:
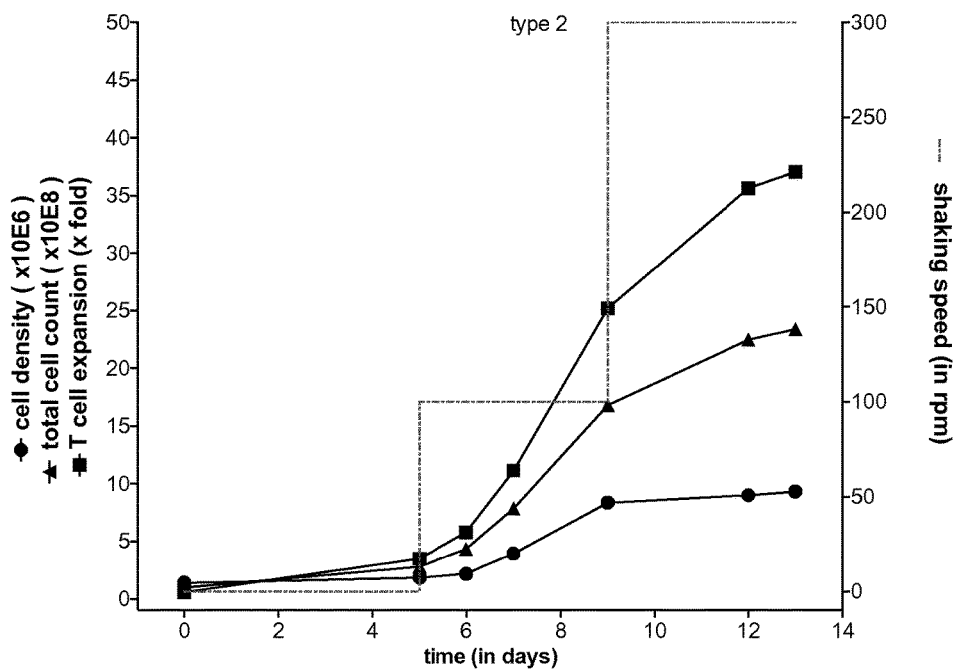
Figure 4C:
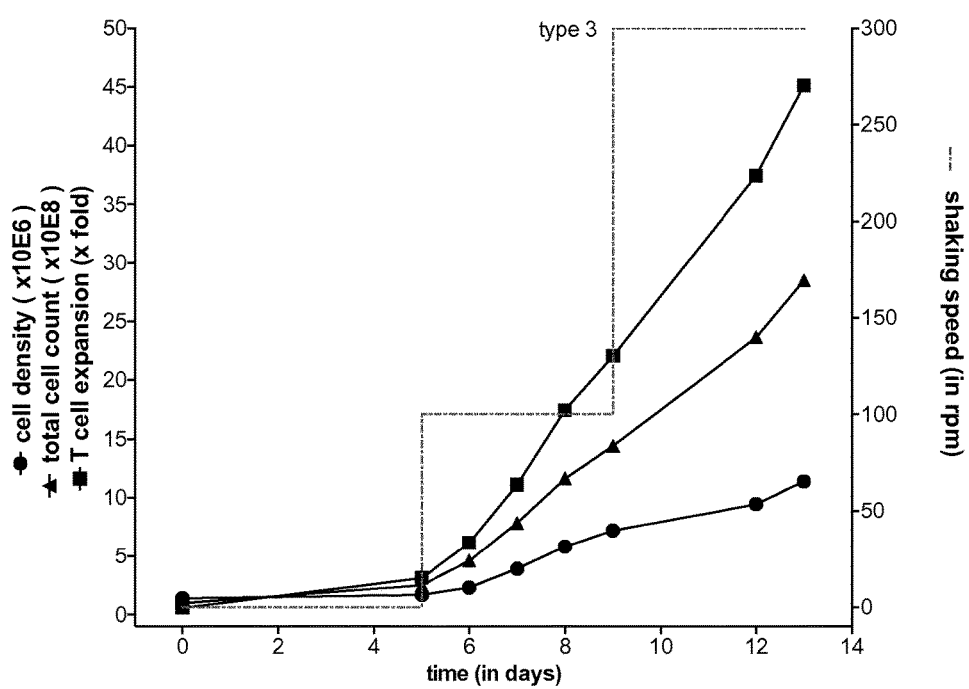

FIG. 4 shows the impact of culture shaking during the manufacturing of gene-engineered T cell. After automated enrichment of CD62L positive cells on the CliniMACS Prodigy®, $1e^8$ enriched T cells were introduced into the chamber, activated with the MACS GMP TransAct CD3/CD28 Kit (Miltenyi Biotec GmbH), gene modified with a lentiviral vector encoding for a chimeric antigen receptor directed against CD20. The first 4-5 days where carried out under steady state cultivation conditions. The culture was then subjected to 3 different types of sporadic shaking modes. A) type 1, every 30 seconds (sec), 100 rpm in one direction for 2 seconds, B) Type 1 from day 5 to day 9. On day 9 Type 2 is activated (every 30 sec, 300 rpm in one direction for 2 seconds) or C) Type 1 from day 5 to day 9. On day 9 Type 3 is activated (every 30 sec, 300 rpm in two directions for 2 seconds). The X axis represents days of culture. The left y axis displays the T cell expansion (squares), the cell density (circles, $1e^6$ cells per ml) and the total cell count (triangles, $\times 1e^8$ cells). The right y-axis displays the shaking speed of the indicated type. As can be seen in C), varying the parameters of the shaking conditions lead to increased cell production.

Figure 5:
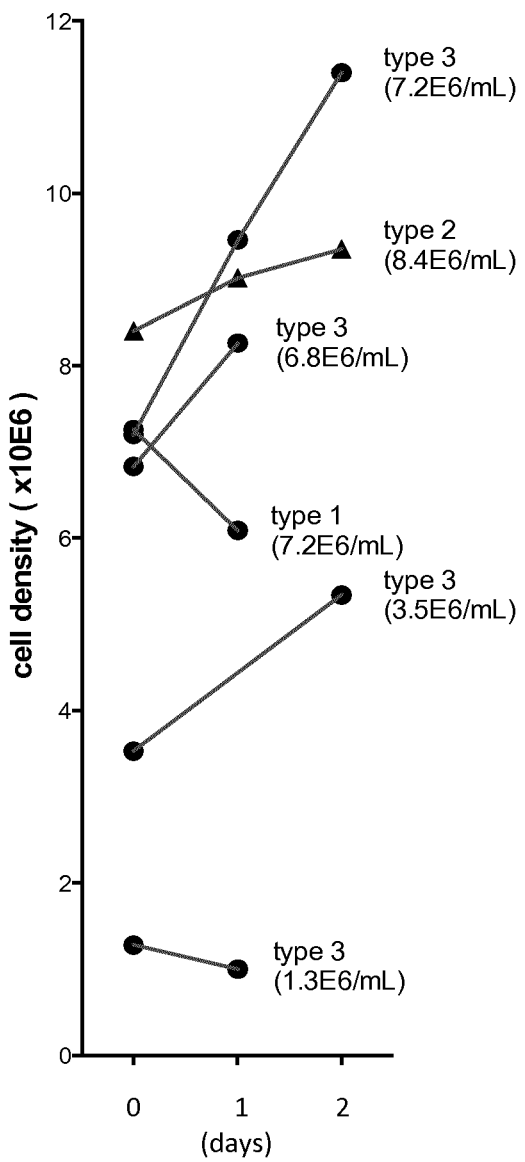
FIG. 5: Relationship between density of the cell culture and effect of the type of shaking applied to the culture

FIG. 5 shows the relationship between density of the cell culture and effect of the type of shaking applied to the culture. Results from several experiments performed in similar conditions as described in FIG. 4, it can be observed that a more robust shaking type (e.g. type 3) will yield better results when subjected to a culture with a density higher than $2e^6$ cells per/ml and preferably higher than $4e^6$ cells/ml. The X-axis, represents days after the culture has been set to 250 ml, in all cases, 8 days after onset of culture and initial T cell activation. The y-axis represents T cell density ($1e^6$ cells/ml).

FIG. 6 shows an in process monitoring of an automated manufacturing run. In order to ensure the T cells are cultured in optimal conditions it is important to be able to sample the culture during the manufacturing run to monitor critical parameters. The automated process described here allows the user to take at any time a sample of the culture medium into dedicated sampling pouches. Parameters such as cell density, glucose, pH etc. can then be measured remotely. The figure represents in process monitoring values of a typical run performed in the CliniMACS Prodigy® using the GMP TexMACS medium (Miltenyi Biotec GmbH). The X-axis represents time in days. The left y axis shows the values of glucose (triangle, in g/ml), pH values (open lozenge). The right Y-axis represents viability (closed lozenge, in %) and shaking speed of the experiment (doted line, in rpm).

Figure 7:
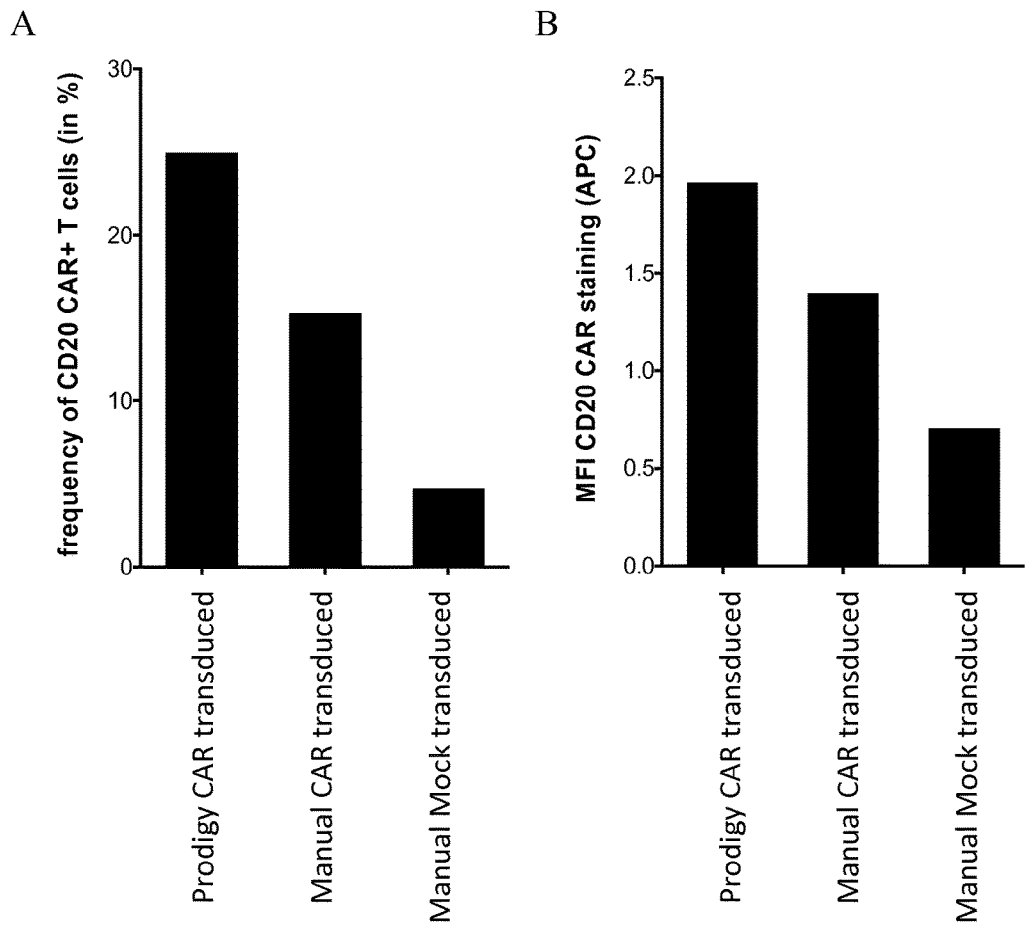

FIG. 7 shows the transduction efficiency in manual versus automated conditions. In similar conditions as described in FIG. 4. $1e^8$ T enriched T cells were stimulated with MACS GMP TransAct CD3/CD28 Kit and transduced with $1e^8$ transducing unit of lentiviral vector encoding or an anti-CD20 chimeric antigen receptor on day 1. In parallel to the automated manufacturing process a manual manufacturing run was carried out. 7 days after transduction a sample was analyzed by flow cytometry to determine A) the frequency of transduced T cells and B) the mean fluorescence intensity of the CAR expression. As can be seen, the percentage of cells expressing the transgene as well as the level of transgene expression is higher in T cells transduced during the automated manufacturing process.

FIG. 8 shows the robustness of automated T cell manufacturing. All lines represent independent automated manufacturing runs performed with different donors. Experiments are performed as described in FIG. 4. The X-axis depicts time in days and the Y-axis the absolute cell count determined on the different days. As can be seen, the automated manufacturing process is very robust and leads to very comparable results from individual runs.

Figure 9A:
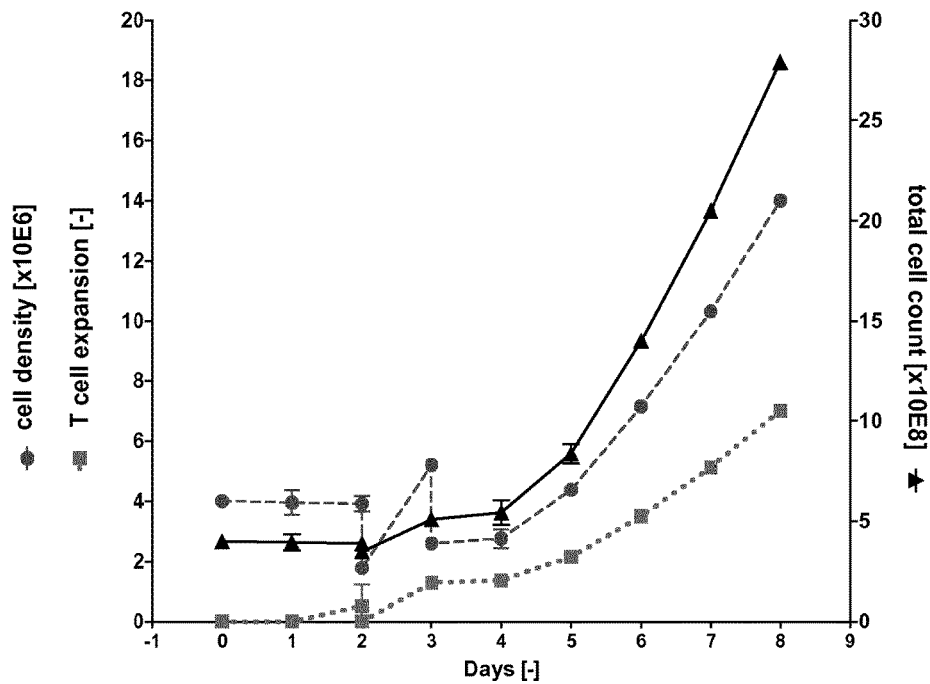
Figure 9B:
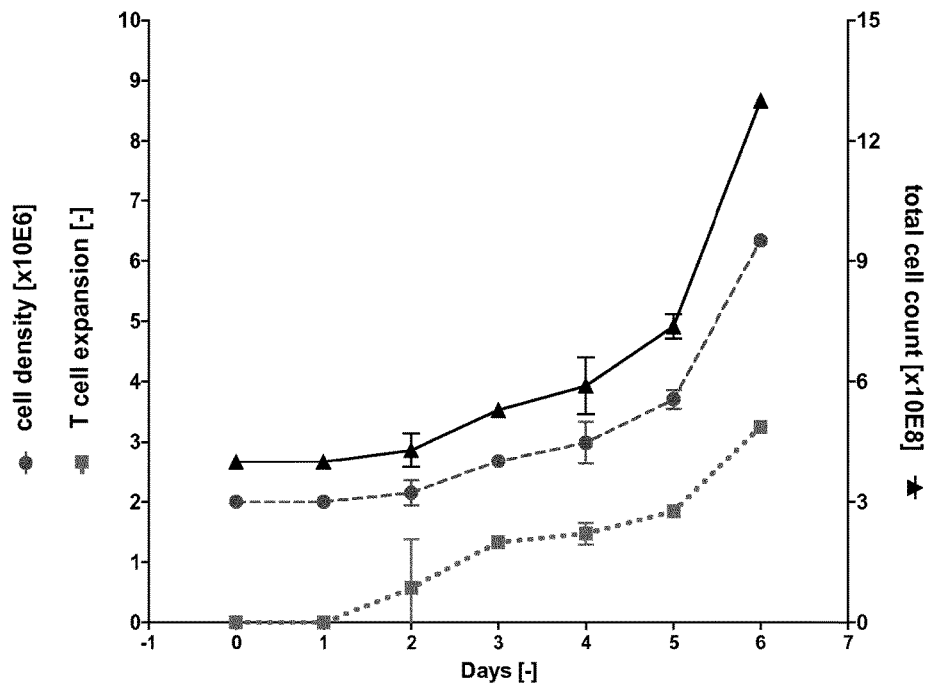

FIG. 9 shows the automated manufacturing using shaking conditions on day 0. CD4/CD8 positive cells were isolated out of apheresis and cultivated in different settings on the CliniMACS Prodigy® platform. A higher density of $4e^8$ cells enriched T cells were seeded in 100 ml (A) or 200 ml (B) total volume on day 0 and culture was immediately carried out under type 3 shaking conditions. The cells in 100 ml were diluted on day 2 and a medium exchange was performed every day beginning on day 4 until end of cultivation. On day 6 the culture started with 200 ml (B) was stopped, the culture beginning with 100 ml (A) was terminated on day 8. Surprisingly, results show that it is possible to activate and expand T cells without a steady state phase during activation at the beginning of the culture. In such dynamic conditions, it is possible to very rapidly generate large numbers of T cells (i.e. $2.8e^9$ T cells on day 8 FIG. 9A, versus $1.8e^9$ total cells on day 8 in FIG. 4C).

FIG. 10 shows a composition of the cell culture during automated manufacturing. A buffy coat from a healthy donor was connected to the tubing set TS520 (Miltenyi Biotec GmbH) installed on the CliniMACS Prodigy®, the naïve and central memory T cell subsets were enriched using the CliniMACS CD62L reagent. $1e^8$ CD62L enriched cells were placed in the culture chamber, activated, transduced on day 1 with a lentiviral vector encoding the green fluorescent protein (GFP) and expanded using the method described in this invention. The figure represents the frequency of the indicated cell subsets (from the bottom of the bars to the top: T cells, B cells, Monocytes, NK cells, NK T cells, and granulocytes). As can be seen after 11 days of culture and in the final harvest sample, the cell product is composed of over 95% of T cells.

EMBODIMENTS

In one embodiment of the invention, a patient sample, for example, comprising T cells, T cell subsets and/or T cell progenitors of interest are introduced into the chamber of a closed and sterile culture system such as the CliniMACS Prodigy®. The sample is centrifugated, preferentially using optical density phase detection, excess erythrocytes are removed, the cell sample is washed using e.g. the CliniMACS Buffer (Miltenyi Biotec GmbH) to avoid cell aggregation, and magnetically labeled with a magnetic cell separation reagent such as CliniMACS CD4 and CD8 Reagent (Miltenyi Biotec GmbH). After labeling, cells are washed, magnetically enriched via an integrated magnetic cell selection column and then returned to a cell culture chamber.

In the cell culture chamber, the T cells can be activated upon steady or shaking culture conditions with one or a combination of reagents capable of inducing T cell proliferation such as agonistic antibodies (e.g. anti-CD3 and anti-CD28), cytokines (e.g. IL-1b, IL-2, IL-4, IL-6, IL-7, IL-9, IL-10, IL-12, IL-15, IL-17, IL-21, IL-22, IL-23, IL-35, TGF-b, IFN alpha, IFN gamma, TNF alpha) recombinant proteins, costimulatory molecules, lectins, ionophores, synthetic molecules, antigen presenting cells (APCs), artificial APCs or feeders. These activation reagents can be provided in solution, coated on the cultivation chamber or coated on a carrier substance present in suspension/solution within the cultivation chamber or on large particles.

T cells can be cultivated upon steady or shaking culture conditions. After a period of culture, viral vector is added to the culture chamber and the cells are transduced. Following a further cell culture period, the cells can be transduced again or washed extensively and harvested (formulated). Prior to in vivo transfer of the gene-modified T cell products the cells can be washed, concentrated and resuspended in a buffer compliant with clinical requirements for in vivo infusion. All steps mentioned above are performed automatically.

In one embodiment of the invention the T cells, T cell subsets and/or T cell progenitors are labeled by binding antibody-coupled magnetic beads to a cell surface marker present on the surface of the T cell, T cell subsets and/or T cell progenitors and enriching the labeled cells by magnetic separation (positive enrichment).

In another embodiment of the invention the T cells, T cell subsets and/or T cell progenitors are enriched by binding antibody-coupled magnetic beads to a cell surface marker not present on the surface of the T cells or defined cellular subsets and depleting the labeled cells by magnetic separation (negative enrichment).

In a further embodiment of the invention in addition to the first enrichment of T cells, T cell subsets and/or T cell progenitors the genetically modified T cells, T cell subsets and/or T cell progenitors are enriched in a second enrichment step by magnetic labeling of the genetically modified T cells, T cell subsets and/or T cell progenitors and magnetic separation before or after cultivation to obtain higher frequency of the genetically modified T cells, T cell subsets and/or T cell progenitors in the finally achieved cell composition obtained by the present method. E.g. if the genetically modified cell is a T cell expressing a CAR or TCR, then the second separation step may be performed by using an antigen-binding molecule coupled to a magnetic particle specific for the recombinantly expressed CAR or TCR on the cell surface of the genetically modified T cell.

In a preferred embodiment of the invention a cell sample, e.g. whole blood from patient, comprising T cells, T cell subsets and/or T cell progenitors is provided. Said sample is connected to a closed and sterile cell culture system, e.g. the sample is connected via tubing sets to the CliniMACS Prodigy® device. The cell sample is prepared by centrifugation in a centrifugation chamber of the device, resulting in the separation of erythrocytes and platelets from other cells including T cells, T cell subsets and/or T cell progenitors. Magnetic separation of T cells, T cell subsets and/or T cell progenitors is performed by using antibodies coupled to magnetic particles specific for markers of T cells, T cell subsets and/or T cell progenitors such as CD2, CD3, CD4, CD8 CD25, CD28, CD27, CD45RA, CD45RO, CD62L, CD95, CD127, CD137, alpha/beta TCR, gamma/delta TCR, CCR7, PD-1 or Lag3. by conducting the labeled cells through a magnet unit with separation column of the device resulting in an enrichment of said T cells, T cell subsets and/or T cell progenitors. After moving the separated T cells, T cell subsets and/or T cell progenitors to the cultivation chamber (which may be identical to the centrifugation chamber) of the device, said cells are set at a given density of $0.5e^6$/ml cells to $2e^6$/ml activated by using modulatory agents, e.g. nanomatrices which consist of mobile polymer chains having attached thereto anti-CD3 and ant-CD28 antibodies or fragments thereof and which are in size between 1 to 500 nm. After said activation of T cells, T cell subsets and/or T cell progenitors said cells are genetically modified in the cultivation chamber of the device, e.g. they are transduced with a lentiviral vector comprising a polynucleotide sequence encoding for a CAR. After genetic modification of the T cells, T cell subsets and/or T cell progenitors said cells are expanded in the cultivation under shaking conditions. Shaking may be performed by sporadic or periodical centrifugation of the cultivation chamber (in this case the cultivation chamber is identical to the centrifugation chamber) under conditions which allow the cells to be in suspension (and as disclosed herein). Finally, the cultured cells are washed by centrifugation, thereby allowing the replacement of culture medium with a buffer appropriate for subsequent applications such as infusion of the generated cell composition to a patient.

In one embodiment of the invention, a higher purity of transduced T cells, e.g. T cells expressing a transgene such as a CAR or TCR on their cell surface, is obtained at the end of the manufacturing process thanks to an additional cell selection step that specifically enriches the gene-modified T cells, this is preferably carried out using magnetic particles coated with antibodies directed against the surface molecule encoded by the transgene. The step of enrichment is preferably carried out by using again the magnetic separation unit of the device in an automated manner and is done before final formulation.

Preferentially, a selection agent that can be completely removed from the surface of the selected cells after this second enrichment and before application to a patient or downstream use is used.

In another embodiment of the invention, it is possible to start the automated manufacturing process with higher cell densities by activating the T cells under suspension conditions. When sufficient numbers of target T cells, T cell subsets and/or T cell progenitors can be obtained from the starting material, it is possible to start the automated manufacturing process with a high cell density of $4e^6$ to $1e^7$ T cells directly under shaking conditions, e.g. using a sporadic or periodical centrifugation of the cultivation chamber (in this case the cultivation chamber is identical to the centrifugation chamber) under conditions which allow the cells to be in suspension for activation of the cells upon onset of the culture. T cells can be further modified using lentiviral vector and expanded under suspension. In this embodiment of the invention, preferentially, the shaking conditions are maintained during the activation, genetic modification and expansion steps of the process as disclosed herein to keep the high density cell culture in suspension. The advantage of such alternative is the possibility to obtain large cell numbers in a shorter period of time (typically 1 week versus 10-14 days).

In one embodiment of the invention the step of genetic modification of the T cells, T cell subsets and/or T cell progenitors may be performed by using lentiviral vectors. Lentiviral vectors with the VSVG pseudotype enable efficient transduction under automated manufacturing method. However the method is entirely suitable for the use of any type of lentiviral vector (with e.g. measles virus (ML-LV), gibbon ape leukaemia virus (GALV), feline endogenous retrovirus (RD114), baboon endogenous retrovirus (BaEV) derived pseudotyped envelopes). Other viral vectors such as gamma or alpha retroviral vectors can be used. Transduction enhancer reagents can be added when necessary using the automated manufacturing described in this invention.

Definitions

Unless defined otherwise, technical and scientific terms used herein have the same meaning as commonly understood by one of ordinary skill in the art to which this invention belongs.

The terms "closed cell sample processing system" and "closed and sterile (cell culture) system" can be used interchangeably.

The term "closed cell sample processing system" as used herein refers to any closed system which reduces the risk of cell culture contamination while performing culturing processes such as the introduction of new material, e.g. by transduction, and performing cell culturing steps such as proliferation, differentiation, activation, and/or separation of cells. Such a system allows to operate under GMP or GMP-like conditions ("sterile") resulting in cell compositions which are clinically applicable. Herein exemplarily the CliniMACS Prodigy® (Miltenyi Biotec GmbH, Germany) is used as a closed cell sample processing system. This system is disclosed in WO2009/072003. But it is not intended to restrict the use of the method of the present invention to the CliniMACS Prodigy®.

The process of the invention may be performed in a closed and sterile system (a closed cell sample processing system), comprising a centrifugation chamber comprising a base plate and cover plate connected by a cylinder, pumps, valves, a magnetic cell separation column and a tubing set. The blood samples or other sources comprising T cells, T cell subpopulations and/or T cell progenitors may be transferred to and from the tubing set by sterile docking or sterile welding. A suitable system is disclosed in WO2009/072003.

The closed cell sample processing system may comprise a plurality of tubing sets (TS) where cells are transferred between TS by sterile docking or sterile welding.

Different modules of the process may be performed in different functionally closed TS with transfer of the product (cells) of one module generated in the one tubing set to another tubing set by sterile means. For example, T cells, T cell subsets and/or T cell progenitors can be magnetically enriched in a first tubing set (TS) TS100 by Miltenyi Biotec GmbH and the positive fraction containing enriched T cells is welded off the TS100 and welded onto a second tubing set TS730 by Miltenyi Biotec GmbH for further activation, modification, cultivation and washing.

The terms "automated method" or "automated process" as used herein refer to any process being automated through the use of devices and/or computers and computer softwares. Methods (processes) that have been automated require less human intervention and less human time. In some instances the method of the present invention is automated if at least one step of the present method is performed without any human support or intervention. Preferentially the method of the present invention is automated if all steps of the method as disclosed herein are performed without human support or intervention other than connecting fresh reagents to the system. Preferentially the automated process is implemented on a closed cell sample processing system such as CliniMACS Prodigy® as disclosed herein.

The closed cell sample processing system may comprise a) a sample processing unit comprising an input port and an output port coupled to a rotating container (or centrifugation chamber) having at least one sample chamber, wherein the sample processing unit is configured to provide a first processing step to a sample or to rotate the container so as to apply a centrifugal force to a sample deposited in the chamber and separate at least a first component and a second component of the deposited sample; and b) a sample separation unit coupled to the output port of the sample processing unit, the sample separation unit comprising a separation column holder, a pump, and a plurality of valves configured to at least partially control fluid flow through a fluid circuitry and a separation column positioned in the holder, wherein the separation column is configured to separate labeled and unlabeled components of sample flown through the column.

Said rotating container may also be used as a temperature controlled cell incubation and cultivation chamber (CentriCult Unit=CCU). This chamber may be flooded with defined gas mixes, provided by an attached gas mix unit (e.g. use of pressurized air/N2/CO2 or N2/CO2/O2).

All agents may be connected to the closed system before process initiation. This comprises all buffers, solutions, cultivation media and supplements, MicroBeads, used for washing, transferring, suspending, cultivating, harvesting cells or immunomagnetic cell sorting within the closed system. Alternatively, such agents might by welded or connected by sterile means at any time during the process.

The cell sample comprising T cells, T cell subsets and/or T cell progenitors may be provided in transfer bags or other suited containers which can be connected to the closed system by sterile means.

The term "providing a cell sample comprising T cells, T cell subsets and/or T cell progenitors" means the provision of a cell sample, preferentially of a human cell sample of hematologic origin. Normally, the cell sample may be composed of hematologic cells from a donor or a patient. Such blood product can be in the form of whole blood, buffy coat, leukapheresis, PBMCs or any clinical sampling of blood product. It may be from fresh or frozen origin.

The term "preparation of the cell sample by centrifugation" as used herein refers to the separation of cells from other components (e.g. non-cell components) of the cell sample provided by centrifugation. The centrifugal step may comprise one, more or all of the following aspects: gradient separation, erythrocyte reduction, platelet removal and cell washing.

The term "washing" means the replacement of the medium or buffer in which the cells are kept. The replacement of the supernatant can be in part (example 50% of the medium is removed and 50% fresh medium is added) this often is applied for dilution or feeding purposes, or entirely. Several washing steps can be combined in order to obtain a more profound replacement of the original medium in which the cells are kept. A washing step often involves pelleting the cells by centrifugation forces and removing the supernatant. In the method of the present invention, cells are pelleted by rotation of the chamber at e.g. 300×g and the supernatant is removed during rotation of the chamber. Medium is added during rotation or at steady state.

The term "shaking conditions" as used herein refers to any means that allow to keep the cells of the cell culture in suspension. The shaking may be performed by rotating (or sporadic centrifugation) a cultivation chamber of a closed and sterile cell culture system, and wherein said rotation is performed periodically as disclosed herein. The shaking may also be performed e.g. by using a whipping equipment, a propelling device or a flow of liquid (e.g channels) integrated into the closed and sterile cell culture system used which prevent sedimentation of the cells.

The term "marker" as used herein refers to a cell antigen that is specifically expressed by a certain cell type. Preferentially, the marker is a cell surface marker so that enrichment, isolation and/or detection of living cells can be performed. The markers may be positive selection markers such as CD4, CD8 and/or CD62L or may be negative selection markers (e.g. depletion of cells expressing CD14, CD16, CD19, CD25, CD56).

The term "expression" as used herein is defined as the transcription and/or translation of a particular nucleotide sequence driven by its promoter in a cell.

The term "particle" as used herein refers to a solid phase surface such as colloidal particles, microspheres, nanoparticles, or beads. Methods for generation of such particles are well known in the field of the art. The particles may be magnetic particles. The particles may be in a solution or suspension or they may be in a lyophilized state prior to use in the present invention. The lyophilized particle is then reconstituted in convenient buffer before contacting the sample to be processed regarding the present invention.

The term "nanostructure" as used herein refers to nano-sized structures which do not fall under the scope of the term "particle" but allow for polyclonal stimulation of T cells when coupled to modulatory agents such as anti CD3- and/or anti CD28-antibodies or fragments thereof.

The nanomatrix as disclosed in WO2014/048920A1 or as given in the MACS GMP TransAct CD3/CD28 Kit (Miltenyi Biotec GmbH, Order no. 170-076-140) is a specific nanostructure.

The term "nanomatrix" as used herein refers to a nanomatrix comprising
  a) a matrix of mobile polymer chains; and
  b) attached to said matrix of mobile polymer chains one or more stimulatory agents which provide activation signals to the T cells; thereby activating and inducing the T cells to proliferate, wherein the nanomatrix is 1 to 500 nm, preferentially 10 to 200 nm, in size. Stimulatory agents may be anti-CD3 and/or anti-CD28 antibodies or fragments thereof.

These polymers consists of mobile (motile), preferentially highly mobile (motile) chains, so the matrix is characterised by the absence of a solid surface as the attachment point for the stimulating agents such as antibodies, and which is in strong contrast to currently used beads or microspheres which regularly have an inflexible, stiff surface.

The matrix consists of a polymeric, preferentially biodegradable or biocompatible inert material which is non-toxic to cells. Preferentially the matrix is composed of hydrophilic polymer chains, which obtain maximal mobility in aqueous solution due to hydration of the chains. The mobile matrix is the only or at least main component of the nanomatrix regardless the agents which are attached thereto.

The mobile matrix may be of collagen, purified proteins, purified peptides, polysaccharides, glycosaminoglycans, or extracellular matrix compositions. A polysaccharide may include for example, cellulose ethers, starch, gum arabic, agarose, dextran, chitosan, hyaluronic acid, pectins, xanthan, guar gum or alginate. Other polymers may include polyesters, polyethers, polyacrylates, polyacrylamides, polyamines, polyethylene imines, polyquarternium polymers, polyphosphazenes, polyvinylalcohols, polyvinylacetates, polyvinylpyrrolidones, block copolymers, or polyurethanes. Preferentially the mobile matrix is a polymer of dextran.

Expamers (Stage Cell Therapeutics, Germany) are another example for a nanostructure. Here, a soluble StrepTactin protein oligomer is functionalized with activating primary ligand such as anti-CD3 and CD28 Fab fragments for polyclonal stimulation of T cell. The StreptTactin backbone allows for a reversible and modular functionalization via association of low-affinity Fab fragments.

The term "antigen-binding molecule" as used herein refers to any molecule that binds preferably to or is specific for the desired target molecule of the cell, i.e. the antigen. The term "antigen-binding molecule" comprises e.g. an antibody or antibody fragment. The term "antibody" as used herein refers to polyclonal or monoclonal antibodies, which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The term "antibody" comprises both intact molecules and antibody fragments, such as Fab, Fab', F(ab')2, Fv and single-chain antibodies. Additionally, the term "antigen-binding molecule" includes any molecule other than antibodies or antibody fragments that binds preferentially to the desired target molecule of the cell. Suitable molecules include, without limitation, oligonucleotides known as aptamers that bind to desired target molecules, carbohydrates, lectins or any other antigen binding protein (e.g. receptor-ligand interaction). The linkage (coupling) between antibody and particle or nanostructure can be covalent or non-covalent. A covalent linkage can be, e.g. the linkage to carboxyl-groups on polystyrene beads, or to NH2 or SH2 groups on modified beads. A non-covalent linkage is e.g. via biotin-avidin or a fluorophore-coupled-particle linked to anti-fluorophore antibody.

The terms "specifically binds to" or "specific for" with respect to an antigen-binding molecule, e.g. an antibody or fragment thereof, refer to an antigen-binding molecule (in case of an antibody or fragment thereof to an antigen-binding domain) which recognizes and binds to a specific antigen in a sample, e.g. CD4, but does not substantially recognize or bind other antigens in said sample. An antigen-binding domain of an antibody or fragment thereof that binds specifically to an antigen from one species may bind also to that antigen from another species. This cross-species reactivity is not contrary to the definition of "specific for" as used herein. An antigen-binding domain of an antibody or fragment thereof that specifically binds to an antigen, e.g. the CD4 antigen, may also bind substantially to different variants of said antigen (allelic variants, splice variants, isoforms etc.). This cross reactivity is not contrary to the definition of that antigen-binding domain as specific for the antigen, e.g. for CD4.

A potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting T cells, T cell subsets and/or T cell progenitors from a cell sample monoclonal antibodies are used in conjunction with colloidal superparamagnetic microparticles having an organic coating by e.g. polysaccharides (Magnetic-activated cell sorting (MACS®) technology (Miltenyi Biotec, Bergisch Gladbach, Germany)). These particles (nanobeads or MicroBeads) can be either directly conjugated to monoclonal antibodies or used in combination with anti-immunoglobulin, avidin or anti-hapten-specific MicroBeads. The MACS® technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s). In case of a positive selection the cells expressing the antigen(s) of interest, which attached to the magnetic column, are washed out to a separate vessel, after removing the column from the magnetic field. In case of a negative selection the antibody used is directed against surface antigen(s), which are known to be present on cells that are not of interest. After application of the cells/magnetic nanoparticles solution onto the column the cells expressing these antigens bind to the column and the fraction that goes through is collected, as it contains the cells of interest. As these cells are non-labeled by an antibody coupled to nanoparticles, they are "untouched". The procedure can be performed using direct magnetic labeling or indirect magnetic labeling. For direct labeling the specific antibody is directly coupled to the magnetic particle. Indirect labeling is a convenient alternative when direct magnetic labeling is not possible or not desired. A primary antibody, a specific monoclonal or polyclonal antibody, a combination of primary antibodies, directed against any cell surface marker can be used for this labeling strategy. The primary antibody can either be unconjugated, biotinylated, or fluorophore-conjugated. The magnetic labeling is then achieved with anti-immunoglobulin MicroBeads, anti-biotin MicroBeads, or anti-fluorophore MicroBeads. The above-described processes can also be performed in a closed cell sample processing system such as CliniMACS® (Miltenyi Biotec GmbH, Germany) or CliniMACS Prodigy® (Miltenyi Biotec GmbH, Germany).

The term "substantially pure cell composition of genetically modified T cells, T cell subsets and/or T cell progenitors" as used herein refers to a cell composition comprising at least 70%, more preferentially at least 90%, most preferentially at least 95% of genetically modified T cells, T cell subsets and/or T cell progenitors in the cell composition obtained by the method of the present invention. The transduction frequency of the cell product depends on the type of vector used to carried out the gene modification as well as the nature of the transgene. Increased frequency of gene-modified T cells can be obtained by including an additional selection step directed towards, at least a part, of the transgene.

"Chimeric antigen receptor" or "CAR" refer to engineered receptors, which graft an antigen specificity onto cells, for example T cells. The CARs of the invention comprise an antigen binding domain also known as antigen targeting region, an extracellular spacer domain or hinge region, a transmembrane domain and at least one intracellular signaling domain or a least one co-stimulatory domain and at least one intracellular signaling domain.

The term "genetically modified cell" means containing and/or expressing a foreign gene or nucleic acid sequence which in turn modifies the genotype or phenotype of the cell or its progeny. Especially, the term refer to the fact that cells can be manipulated by recombinant methods well known in the art to express stably or transiently peptides or proteins, e.g. CARs which are not expressed in these cells in the natural state. Genetic modification of cells may include but is not restricted to transfection, electroporation, nucleofection, transduction using retroviral vectors, lentiviral vectors, non-integrating retro- or lentiviral vectors, transposons, designer nucleases including zinc finger nucleases, TALENs or CRISPR/Cas.

The genetically modified T cells, T cell subsets and/or T cell progenitors obtainable by the methods disclosed herein may be used for subsequent steps such as research, diagnostics, pharmacological or clinical applications known to the person skilled in the art.

The genetically modified T cells, T cell subsets and/or T cell progenitors can also be used as a pharmaceutical composition in the therapy, e.g. cellular therapy, or prevention of diseases. The pharmaceutical composition may be transplanted into an animal or human, preferentially a human patient. The pharmaceutical composition can be used for the treatment and/or prevention of diseases in mammals, especially humans, possibly including administration of a pharmaceutically effective amount of the pharmaceutical composition to the mammal. Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The term "therapeutic effective amount" means an amount which provides a therapeutic benefit for the patient.

The composition of genetically modified T cells, T cell subsets and/or T cell progenitors obtained by the method of the present invention may be administered either alone, or as a pharmaceutical composition in combination with diluents and/or with other components such as cytokines or cell populations. Briefly, pharmaceutical compositions of the present invention may comprise the genetically modified T cells, T cell subsets and/or T cell progenitors of the present invention as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

EXAMPLES

Example 1: Automated Manufacturing of Gene-Modified T Cells Using Several Closed Sterile Tubing Sets A leukapheresis bag (100-200 ml) from a donor is connected, by sterile welding to the Tubing set TS 100 (Miltenyi Biotec GmbH) installed on the CliniMACS Prodigy® device. CliniMACS buffer as well as CliniMACS CD4 and CD8 reagents (Miltenyi Biotec GmbH) are also connected to the same Tubing set. An enrichment program is launched. The tubing set is automatically primed with buffer, then the leukaphereis product is transferred to the chamber of the tubing set where it is washed 3 times with CliniMACS buffer in order to remove serum and platelets. A red cell reduction is also performed to remove excess erythrocytes. The CliniMACS CD4 and CD8 reagents are transferred to the cells into the chamber for magnetic labeling of the CD4 and CD8 positive cells. After 30 min incubation at room temperature, the magnetically labeled cells are automatically transferred onto a column placed in a magnetic field. The labeled cells are trapped and the non-labeled cells are eluted in a non-target cell fraction bag. The column with the labeled cells is rinsed several times after which the labeled cells are eluted into the target cell fraction bag. A sample pouch integrated in the tubing set allows to obtain a sample of 1-2 ml that is analyzed remotely for cell counts and cell purity by flow cytometry (FIG. 12). Part of the enriched cells are transferred (via sterile welding connection) into another Tubing set (TS730) newly installed on a CliniMACS Prodigy® device. The tubing set is also connected to MACS GMP TexMACS medium supplemented with IL-2, MACS GMP TransAct CD3/CD28 Kit (all Miltenyi Biotec GmbH) and $1e^8$ enriched T cells. The activation program is started. The enriched cells are washed and resuspended in medium, the culture is set at 37° C. and with a 5% CO2 gas supply. Upon equilibration of the culture, the activation reagent is automatically added to the culture. 24$h$ later, a sample is analyzed for the upregulation of the activation markers CD25 and CD69 (FIG. 2). A bag containing the viral vector is sterile welded onto the tubing set using for instance a Terumo sterile welder, the user acknowledges the prompt in the software asking for confirmation that the viral vector has been connected and the viral vector is transferred into the chamber containing the activated T cells. After 5 days of culture the T cells are transferred into a 5 liter bag and transferred onto the Wave Bioreactor™ (Life Technologies), another device enabling T cell expansion. The cells are cultured for an additional 7 days in suspension. The bag of expanded cells is connected back onto a fresh tubing set on the CliniMACS Prodigy®. The CliniMACS Prodigy® allows the automated concentration of the cells from 5 L down to 100 ml and the re-buffering of the cells in a solution suitable for human infusion.

Example 2: Automated Manufacturing of Gene-Modified T Cells Using a Single Closed Sterile Tubing Set A buffy coat bag of 100-200 ml from a donor is connected, by sterile welding to the Tubing set TS520 (Miltenyi Biotec GmBH) installed on the CliniMACS Prodigy® device. CliniMACS buffer as well as CliniMACS CD62L reagent, MACS GMP CD3/CD28 Kit and MACS GMP TexMACS medium containing 10 ng/ml IL-7 and IL-15, are also connected to the TS520 (all Miltenyi Biotec GmbH). The activity matrix is then filled with activities (e.g. transduction, feed, wash, final formulate) and their parameters (e.g. day, volume, temperature) of the automated manufacturing run. The programmed software is then launched (FIG. 3). As in example 1 the leukapheresis is washed. Labeling takes place at 4-8° C. (this is important in order to enrich CD62L positive cells as CD62L is shed from the surface of cells at room temperature). Labeled cells are enriched and eluted into a reapplication bag which is part of the tubing set. The program asks for a sample to be taken (using sampling pouches included in the tubing set). Once the cell density determined, this information is indicated in the program as well as the required number of cells to be transferred back into the chamber (e.g. 1e8). The required volume of enriched cells containing $1e^8$ enriched cells is then automatically transferred into the cultivation chamber. The activation reagent is then added to the culture. On day 1, the bag containing the Lentiviral vector in 10 ml is connected to the tubing set (this is performed extemporaneously due to the short half life of viral vectors). The viral vector, in this case a lentiviral vector encoding a CD20 CAR (comprising the 4-1BB and CD3zeta signaling domains) is then transferred onto the activated T cells. The T cells remain in culture at 37° C. and in an atmosphere enriched with 5% CO2 for an additional 2 days. On day 5 the spent culture medium is automatically washed away and replaced with fresh medium. The culture is now set on type 1 shaking (low shaking) in order to gently resuspend the T cells using a sporadic slow shaking of the chamber. Half the culture medium is exchanged every other day in order to feed the cells with fresh medium. On day 9 the shaking speed is increased to a type 3 shaking (more vigorous resuspension). On days 11-13, the manufacturing process reaches an end, the cells are washed several time with a solution suitable for human infusion (i.e. final formulation buffer) and harvested in a bag for further clinical handling (FIGS. 4 and 6). Either for direct infusion or for cryopreservation. The manufactured gene-modified T cells were analyzed for their cell composition (FIG. 10), their percent of transduced cells and the level of transgene expression per transduced cells (FIGS. 7A and B respectively).

Example 3: Automated Manufacturing of Gene-Modified T Cells Starting with High Density Culture Activated Under Shaking Conditions Starting from a leukapheresis of 100-200 ml, CD4 and CD8 T cells are enriched similarly to Example 2 using the tubing set TS520 installed onto the CliniMACS Prodigy®. In this example however a high density of $4e^6$ enriched T cells/ml are transferred into the chamber of the closed sterile tubing set. The enriched T cells were seeded in 100 ml (FIG. 9A) on day 0 and activation was immediately carried out under type 3 shaking conditions using MACS GMP TransAct CD3/CD28 kit and 200IU IL-2 in MACS GMP TexMACS medium. The cells in 100 ml were diluted on day 2 and a medium exchange was performed every day beginning on day 4 until end of cultivation. The cultivation was ended on day 8. Surprisingly, results show that it is possible to activate and expand T cells without a steady state phase during activation at the beginning of the culture. In such dynamic conditions, it is possible to very rapidly generate large numbers of T cells (i.e. $2.8e^9$ T cells on day 8 FIG. 8A, versus $1.8e^9$ total cells on day 8 in FIG. 4C).

Example 4: Automated Manufacturing of Gene-Modified T Cells Starting from Frozen Leukapheresis A 100 ml bag of frozen leukapheresis from a donor was thawed and transferred into a 3 L MACS GMP Cell Differentiation bag (Miltenyi Biotec GmbH product) and diluted with MACS GMP TexMACS medium into 2 L. Thawed cells were rested for 48 hours at 37° C. in 5% CO2, the bag of cells was then connected to a closed sterile tubing set installed on the CliniMACS Prodigy® for automated cell concentration. A similar manufacturing process as described on Example 2 was then carried out (using CD62L enriched T cells). On day 12, the gene modified T cells were final formulated in 100 ml CliniMACS Buffer and transferred into the harvest bag. The entire bag was connected by sterile welding to the closed sterile tubing set TS100 installed on a CliniMACS® Prodigy. There, the gene-modified T cells where labeled with anti-IgG1 microbead in order to permit isolation of gene-modified T cells from the non-modified T cells. All steps from the diluted and rested thawed cells to the manufacturing and isolation of gene-modified T cells was performed in an automated manner using several different tubing sets and several different types of programs.

The invention claimed is:
1. A process for generation of genetically modified T cells, T cell subsets and/or T cell progenitors comprising the steps:

a) providing a cell sample comprising T cells, T cell subsets and/or T cell progenitors;
b) preparation of the cell sample by centrifugation;
c) magnetic separation of the T cells, T cell subsets and/or T cell progenitors, to thereby provide enriched T cells, T cell subsets and/or T cell progenitors;
d) activation of the enriched T cells, T cell subsets and/or T cell progenitors using modulatory agents, to thereby provide activated T cells, T cell subsets and/or T cell progenitors;
e) genetic modification of the activated T cells, T cell subsets and/or T cell progenitors, to thereby provide genetically modified T cells, T cell subsets and/or T cell progenitors; and
f) expansion of the genetically modified T cells, T cell subsets and/or T cell progenitors in a cultivation chamber, to thereby provide cultured T cells, T cell subsets and/or T cell progenitors; and
g) washing of the cultured T cells, T cell subsets and/or T cell progenitors, characterized in that all steps are performed within a closed and sterile cell culture system, and wherein expansion step (f) is performed under shaking conditions.

2. The process according to claim 1, wherein activation is performed using T cell, T cell subsets and/or T cell progenitor densities from between $0.5e^6$ cells/mL to $4e^6$ cells/mL during activation.

3. The process according to claim 1, wherein activation is performed using high T cell, T cell subsets and/or T cell progenitor densities from between $4e^6$ cells/mL to $1e^7$ cells/mL during activation.

4. The process according to claim 1, wherein genetic modification comprises introducing into the activated T cells, T cell subsets and/or T cell progenitors a polynucleotide sequence encoding a chimeric antigen receptor (CAR) or a T cell receptor (TCR).

5. A process for generation of genetically modified T cells, T cell subsets and/or T cell progenitors comprising the steps:
a) providing a cell sample comprising T cells, T cell subsets and/or T cell progenitors
b) preparation of the cell sample by centrifugation;
c) magnetic separation of the T cells, T cell subsets and/or T cell progenitors, to thereby provide enriched T cells, T cell subsets and/or T cell progenitors;
d) activation of the enriched T cells, T cell subsets and/or T cell progenitors using modulatory agents, to thereby provide activated T cells, T cell subsets and/or T cell progenitors;
e) genetic modification of the activated T cells, T cell subsets and/or T cell progenitors, to thereby provide genetically modified T cells, T cell subsets and/or T cell progenitors, wherein the genetic modification is a polynucleotide sequence encoding for a chimeric antigen receptor (CAR) or a T cell receptor (TCR), and wherein the genetically modified T cells, T cell subsets and/or T cell progenitors express the CAR or the TCR;
f) expansion of the genetically modified T cells, T cell subsets and/or T cell progenitors in a cultivation chamber, to thereby provide cultured T cells, T cell subsets and/or T cell progenitors; and
g) washing the cultured T cells, T cell subsets and/or T cell progenitors, wherein all steps are performed within a closed and sterile cell culture system, and wherein the genetically modified cells expressing the CAR or the TCR are separated from cells not expressing the CAR or the TCR in an additional magnetic separation step before step (g) is performed.

6. The process according to claim 1, wherein the modulatory agents are selected from the group consisting of: agonistic antibodies, cytokines, recombinant costimulatory molecules and small drug inhibitors.

7. The process according to claim 1, wherein the modulatory agents are anti-CD3 and anti-CD28 antibodies or fragments thereof coupled to beads or nanostructures.

8. The process according to claim 7, wherein the nanostructures are nanomatrices, wherein the nanomatrices comprise a matrix of mobile polymer chains attached to anti-CD3 and anti-CD28 antibodies or fragments thereof, and wherein the nanomatrices are 1 to 500 nm in size.

9. The process according to claim 1, wherein genetic modification is performed by transducing the activated T cells, T cell subsets and/or T cell progenitors with lentiviruses, gamma-retroviruses, alpha-retroviruses or adenoviruses, by electroporation, or by transfection of nucleic acids, proteins, site-specific nucleases, self-replicating RNA viruses or integration-deficient lentiviral vectors.

10. The process according to claim 1, wherein the genetic modification of T cells, T cell subsets and/or T cell progenitors is performed by transducing the activated T cells, T cell subsets and/or T cell progenitors with lentiviral vectors.

11. The process according to claim 1, wherein the magnetic separation of the T cells, T cell subsets and/or T cell progenitors is performed using antigen-binding molecules specific for a cell surface marker on the surface of the T cells, T cell subsets and/or T cell progenitors and coupled to magnetic particles.

12. The process of claim 11, wherein the cell surface marker is selected from the group consisting: CD2, CD3, CD4, CD8 CD25, CD28, CD27, CD45RA, CD45RO, CD62L, CD95, CD127, CD137, alpha/beta TCR, gamma/delta TCR, CCR7, PD-1 and Lag3.

13. The process according to claim 5, wherein the modulatory agents are selected from the group consisting of: agonistic antibodies, cytokines, recombinant costimulatory molecules and small drug inhibitors.

14. The process according to claim 5, wherein the genetic modification is performed by transducing the activated T cells, T cell subsets and/or T cell progenitors with lentiviruses, gamma-retroviruses, alpha-retroviruses or adenoviruses, by electroporation, or by transfection of nucleic acids, proteins, site-specific nucleases, self-replicating RNA viruses or integration-deficient lentiviral vectors.

15. The process according to claim 5, wherein the activation is performed using T cell, T cell subsets and/or T cell progenitor densities from between $0.5e^6$ cells/mL to $4e^6$ cells/mL during activation.

16. The process according to claim 5, wherein the activation is performed using high T cell, T cell subsets and/or T cell progenitor densities from between $4e^6$ cells/mL to $1e^7$ cells/mL during activation.

* * * * *

UNITED STATES PATENT AND TRADEMARK OFFICE
CERTIFICATE OF CORRECTION

PATENT NO. : 10,131,876 B2
APPLICATION NO. : 15/305597
DATED : November 20, 2018
INVENTOR(S) : Andrew Kaiser, Mario Assenmacher and Ian Johnston Page 1 of 1

It is certified that error appears in the above-identified patent and that said Letters Patent is hereby corrected as shown below:

In the Claims

Column 19, Line 41, Claim 5, after "progenitors" insert -- ; --;

Column 20, Line 38, Claim 12, delete "CD8" and insert -- CD8, --.

Signed and Sealed this
Twenty-sixth Day of May, 2020

Andrei Iancu
*Director of the United States Patent and Trademark Office*